United States Patent [19]
Arraudeau et al.

[11] Patent Number: 5,925,337
[45] Date of Patent: Jul. 20, 1999

[54] WATERPROOF COMPOSITION FOR COVERING THE EYELASHES, AND PROCESS FOR THE PREPARATION THEREOF

[75] Inventors: Jean-Pierre Arraudeau; Jeanne Patraud, both of Paris; Bertrand Piot, La Garenne Colombes, all of France

[73] Assignee: L'Oreal, Paris, France

[21] Appl. No.: 08/110,996

[22] Filed: Aug. 24, 1993

Related U.S. Application Data

[63] Continuation of application No. 07/730,825, Sep. 10, 1991., abandoned

[30] Foreign Application Priority Data

Mar. 1, 1990 [FR] France .................................. 90 02578

[51] Int. Cl.⁶ ........................... A61K 7/03; A61K 7/032; A61K 7/06; A61K 7/48
[52] U.S. Cl. ............................................................. 424/63
[58] Field of Search ................................................ 424/63

[56] References Cited

U.S. PATENT DOCUMENTS

| | | |
|---|---|---|
| 4,336,246 | 6/1982 | Leon-Pekarek . |
| 4,423,031 | 12/1983 | Murui et al. . |
| 4,871,536 | 10/1989 | Arraudeau et al. . |
| 4,988,502 | 1/1991 | Ounanian et al. . |
| 5,053,220 | 10/1991 | Arraudeau et al. ....................... 424/63 |
| 5,053,221 | 10/1991 | Robertson et al. . |
| 5,154,916 | 10/1992 | Arraudeau et al. ....................... 424/63 |
| 5,356,627 | 10/1994 | Cunha et al. ........................... 424/401 |

FOREIGN PATENT DOCUMENTS

| | | |
|---|---|---|
| 2528699 | 12/1983 | France . |
| 2124081 | 2/1984 | United Kingdom . |
| 2167301 | 5/1986 | United Kingdom . |
| 2216797 | 10/1989 | United Kingdom . |

OTHER PUBLICATIONS

WPI, File Supplier, Derwent Publication Ltd., AN–83–829918.

*Primary Examiner*—Robert H. Harrison
*Attorney, Agent, or Firm*—Nixon & Vanderhye, P.C.

[57] ABSTRACT

This composition, containing in the conventional manner at least one wax, at least one thickening agent and at least one volatile organic solvent and optionally other conventional ingredients (fillers, pigments, vitamins, amino acids, etc.) is characterized in that it contains an aqueous solution of at least one water-soluble film forming polymer (keratin, chitin, chitosan or cellulose derivatives, acrylic polymers, polyvinyl pyrrolidones and vinylic copolymers, natural polymers, ethylene polymers and oxy-ethylenated silicones, etc.). The originality of this mascara consists in obtaining an increase in the water resistance of the product by introducing an aqueous solution of water-soluble substances into an anhydrous formula. The system does not contain an emulsifying agent, but nevertheless allows for a stable composition containing approximately 10% of water in a completely hydrophobic medium.

10 Claims, No Drawings

WATERPROOF COMPOSITION FOR COVERING THE EYELASHES, AND PROCESS FOR THE PREPARATION THEREOF

This is a continuation of application Ser. No. 07/730,825, filed Sep. 10, 1991, abandoned.

This invention relates to a waterproof cosmetic composition for covering the eyelashes. When intended for make-up for the eyelashes, a composition of this kind generally contains pigments and is then referred to as "mascara". If it does not comprise pigments, it simply constitutes a make-up foundation or base for the eyelashes. This invention also relates to a process for the preparation of this new composition.

The waterproof mascaras on the market at present are anhydrous products based on non-aqueous organic solvents. The major disadvantage of these mascaras is the fact that they have indifferent stretching properties, in all cases lower than those of non-waterproof mascaras. There are also waterproof mascaras in the form of water in oil emulsions. However, their water resistance is unsatisfactory.

The applicants have found in a quite surprising manner that when an aqueous solution of at least one water-soluble film forming polymer is introduced into a typical anhydrous waterproof mascara composition, it is possible to increase considerably the water resistance of the mascara, to obtain simultaneously a composition which, although containing water in a completely hydrophobic medium, is stable without the presence of an emulsifying agent, and also to obtain a mascara having cosmetic properties superior to those of the waterproof mascaras known to date, particularly from the point of view of rapidity of making up, ease of application, stretching and bending of the eyelashes. It should be noted that adding the film forming polymer in the absence of water does not improve the properties of the mascara. It is therefore necessary for water to be present in the film forming polymer.

The introduction of an aqueous solution of water-soluble substances or of water into normally anhydrous cosmetic products has already been described, particularly in Japanese Patent Application No. 61/83110, although this document relates to a cosmetic product for cutaneous application, particularly a lipstick, the aim of which is to provide moisturizing substances and to apply a thick moist film to the lips. According to this document, water or an aqueous solution of a water-soluble substance is dispersed in a lipstick or a lipstick base in the presence of one or more dispersing agents selected from cholesterol, phytosterols, phospholipids and saponins. The presence of dispersing agents such as sterols is essential for the production and stability of these products, as the said dispersing agents make it possible to incorporate the aqueous phase in the anhydrous base.

It has been proven that the cosmetic composition constituting make-up for the eyelashes according to the invention can in fact be produced in the absence of sterols, although these may still be present in the formula in very low concentrations by way of waxes.

Therefore, this invention relates to the new industrial product formed by a waterproof composition for covering the eyelashes; containing at least one wax, at least one thickening agent, and at least one volatile organic solvent, characterized in that it moreover contains an aqueous solution of at least one water-soluble film forming polymer.

The film forming polymer (or polymers) is (are) selected, in particular, from the group formed by:

keratin derivatives, such as keratin hydrolysates and sulphonic keratins;

anionic, cationic, amphoteric or non-ionic derivatives of chitin or chitosan;

cellulose derivatives, such as hydroxyethyl cellulose, hydroxypropyl cellulose, methyl cellulose, ethyl hydroxyethyl cellulose, carboxy-methyl cellulose, and quaternised derivatives of cellulose;

acrylic polymers, such as polyacrylates and polymethacrylates, and acrylic copolymers;

polyvinyl pyrrolidones and vinylic copolymers, such as the copolymer of methyl vinyl ether and maleic anhydride or the copolymer of vinyl acetate and crotonic acid;

natural polymers, such as:
 gum arabic, guar gum, xanthan derivatives and karaya gum;
 alginates and carragheenates;
 glycoaminoglycanes, hyaluronic acid and derivatives thereof;

ethylene polymers, such as polyethylene glycols, and oxy-ethylenated silicones.

The concentration of water-soluble film forming polymer (s) in the aqueous solution is, in particular, between approximately 0.1 and 55% by weight of active ingredients and the concentration of the aqueous phase in relation to the total weight of the composition is, in particular, between approximately 1 and 35% by weight.

The wax (or waxes) is (are) selected, in particular, from animal, vegetable, mineral and synthetic waxes and the various fractions of natural waxes, all of these waxes as a general rule having a melting point of between 60 and 110° C. and a needle penetration at 25° C. of between approximately 3 and 40, as measured according to US standard ASTM DS or according to French standard NFT 004. The principle of the measurement of the penetration of a needle according to these two standards consists in measuring the depth of penetration, expressed in tenths of a millimeter, of a standardized needle (weighing 2.5 g, placed in a needle holder weighing 47.5 g, i.e. a total of 50 g) placed on the wax for 5 seconds.

Among the animal waxes that can be used are, inter alia, beeswaxes, lanolin waxes and Chinese waxes. Possible vegetable waxes are, inter alia, carnauba waxes, candelilla waxes, ouricury waxes, cork fiber waxes, sugar cane waxes and Japan waxes. Possible mineral waxes are, in particular, paraffins, microcrystalline waxes; lignite waxes (Montanwachs) and ozokerites. Possible synthetic waxes are, in particular, polyethylene waxes, waxes obtained by the Fischer-Tropsch process and wax-like polymers and esters thereof. All of these waxes are well known to the person skilled in the art.

The wax (or waxes) used according to the invention is (are) preferably solid and rigid at a temperature below 50° C. In addition, the wax concentration, in relation to the total weight of the composition, is, in particular, between approximately 2 and 40% by weight.

The thickening agent (or agents) is (are) selected, in particular, from the group formed by organically modified clays, such as montmorillonites and hectorite derivatives, e.g. bentonite. The concentration of thickening agent(s) in relation to the total weight of the composition is, in particular, between approximately 5 and 15% by weight.

The volatile organic solvent (or solvents) is (are) selected, in particular, from the group formed by isoparaffin, turpentine oil, isopropyl alcohol, ethyl alcohol, white spirit and volatile silicone derivatives. The concentration of volatile organic solvent(s) in relation to the total weight of the composition is, in particular, between approximately 35 and 50% by weight.

Moreover, the composition according to the invention may also contain up to 10% by weight, in relation to the total weight of the composition, of at least one filler. Fillers are essentially adapted to increase the covering properties of the product and are, in particular, powders generally used in cosmetic products, such as talc, starch, kaolin and polyamides.

The composition according to the invention may also contain at least one pigment, in a proportion that may be up to 20% by weight in relation to the total weight of the composition, depending on the coloration and intensity of coloration it is desired to obtain. However, as indicated hereinabove, it may also be envisaged to produce a composition without pigments, this then constituting a make-up foundation for the eyelashes or a waterproof base for the eyelashes.

The pigments that can be used are selected, in particular, from mineral pigments, organic pigments, pearl pigments and coated pigments.

The following are examples of mineral pigments:

titanium dioxide (rutile or anatase), possibly surface-treated, and classified in the Color Index under the reference CI 77891;

black, yellow, red and brown iron oxides, classified under the references CI 77499, 77492, 77491;

manganese violet (CI 77742);

ultramarine (CI 77007);

chromium oxide (CI 77288);

chromium hydrate (CI 77289), and iron blue (CI 77510).

Possible organic pigments are, in particular, the pigments certified by the FOOD & DRUG ADMINISTRATION in the United States of America under the names:

D & C red n° 19 (CI 45170);

D & C red n° 9 (CI 15585);

D & C red n° 30 (CI 73360);

D & C red n° 3 (CI 45430);

D & C red n° 21 (CI 45380);

D & C red n° 27 (CI 45410);

D & C red n° 13 (CI 15630);

D & C red n° 7 (CI 15850-1);

D & C red n° 6 (CI 15850-2);

D & C red n° 36 (CI 12085);

D & C orange n° 10 (CI 45425);

D & C orange n° 4 (CI 15510);

D & C orange n° 5 (CI 45370);

D & C yellow n° 6 (CI 15985);

D & C yellow n° 5 (CI 19140), and carbon black (CI 77266), and lacquers based on cochineal carmine (CI 75470).

Pearl pigments may be selected, in particular, from:

white pearl pigments, such as mica covered in titanium oxide, bismuth oxychloride;

colored pearl pigments, such as titanium mica with iron oxides, titanium mica with iron blue or chromium oxide, titanium mica with an organic pigment of the aforesaid type and those based on bismuth oxychloride;

coated pigments, such as those obtained from the pigments listed hereinabove and the surface of which has been treated with various substances, e.g. amino acids, silicones, metallic salts or collagen.

In addition to the components mentioned hereinbefore, the compositions according to the invention may also contain ingredients used in a conventional manner in make-up compositions for the eyelashes and selected, in particular, from softening agents, preservatives, sequestering agents, perfumes, binding agents, oils, silicones, cohesive agents, non-film forming polymers, alkalizing or acidifying agents, and agents noted for their beneficial effect on the eyelashes, such as vitamins or amino acids.

This invention also relates to a process for the preparation of a waterproof composition for covering the eyelashes as defined hereinabove, this process being characterised in that:

in a first stage, the components of the fatty phase and any lipid-soluble additives are mixed;

in a second stage, the fillers and/or any pigments, and then the volatile organic solvent (or solvents) are added to the mixture obtained in this manner, and in a third stage, the aqueous phase containing the water-soluble film forming polymer (or polymers) and any additives and/or water-soluble active ingredients are dispersed in the resulting mixture.

The object of the invention will be more readily understood from the following description of several embodiments, given purely by way of non-limiting examples. Examples 1 to 9 are examples of the formulation of different mascaras prepared according to the general method of operation described hereinabove. Although these mascaras do not contain an emulsifying agent, they are stable. They were applied to the eyelashes by the users and all gave satisfaction. Examples 10 to 12 describe comparative tests and the results, comparing mascaras of the invention with a conventional waterproof mascara, the difference being the presence in the former of an aqueous solution of a water-soluble film forming polymer.

Example 1

A waterproof mascara was prepared according to the following formula:

| | |
|---|---|
| Paraffin wax | 12 g |
| Lanolin alcohol | 15 g |
| Starch | 2 g |
| Iron oxide | 5 g |
| Isoparaffin | 45 g |
| Montmorillonite | 8 g |
| Panthenol | 3 g |
| Chitosonium carboxylate pyrrolidone, sold under the name "KYTAMER PC" by "AMERCHOL" | 3 g |
| Water | 7 g |
| Preservatives | qs |

Example 2

A waterproof mascara was prepared according to the following formula:

| | |
|---|---|
| Carnauba wax | 12 g |
| Lanolin alcohol | 15 g |
| Starch | 2 g |
| Iron oxide | 5 g |
| Isoparaffin | 45 g |
| Montmorillonite | 8 g |
| Keratin hydrolysate, sold under the name "KERASOL" by "CRODA CHEMICALS" | 2.5 g |

Example 3

A waterproof mascara was prepared according to the following formula:

| | |
|---|---|
| Natural beeswax | 12 g |
| Paraffin | 15 g |
| Starch | 2 g |
| Iron oxide | 5 g |
| Isoparaffin | 45 g |
| Montmorillonite | 8 g |
| Cysteine | 0.5 g |
| Hydroxy proline | 0.5 g |
| Vinylimidazolinium methochloride/vinyl pyrrolidone copolymer (ratio by weight: 30/70), sold under the name "LUVIQUAT FC 370" by "BASF" | 4 g |
| Water | 8 g |
| Preservatives | qs |

Example 4

A waterproof mascara was prepared according to the following formula:

| | |
|---|---|
| Paraffin | 12 g |
| Lanolin alcohol | 15 g |
| Talc | 2 g |
| Iron oxide | 5 g |
| Isoparaffin | 45 g |
| Montmorillonite | 8 g |
| Acrylamide/dimethyl diallylammonium chloride copolymer in solution in water, dry matter content 7%, sold under the name "MERQUAT 550" by "MERCK" | 2 g |
| Water | 11 g |
| Preservatives | qs |

Example 5

A waterproof mascara was prepared according to the following formula:

| | |
|---|---|
| Modified beeswax | 10 g |
| Paraffin | 10 g |
| Starch | 2 g |
| Iron oxide | 7 g |
| Isoparaffin | 50 g |
| Montmorillonite | 8 g |
| Hydroxyethyl cellulose/diallyl dimethyl ammonium chloride, sold under the name "CELQUAT L200" by "NATIONAL STARCH" | 1.5 g |
| Water | 11.5 g |
| Preservatives | qs |

Example 6

A waterproof mascara was prepared according to the following formula:

| | |
|---|---|
| Natural beeswax | 10 g |
| Paraffin | 6 g |
| Ozokerite | 6 g |
| Talc | 2 g |
| Iron oxide | 5 g |
| Montmorillonite | 8 g |
| Isoparaffin | 50 g |
| Vinyl pyrrolidone/vinyl acetate copolymer, sold under the name "PVP/VA W-735" by "GAF CORP" | 3 g |
| Water | 10 g |
| Preservatives | qs |

Example 7

A waterproof mascara was prepared according to the following formula:

| | |
|---|---|
| Paraffin wax | 10 g |
| Lanolin alcohol | 13 g |
| Starch | 2 g |
| Iron oxide | 5 g |
| Isoparaffin | 41.5 g |
| Montmorillonite | 8 g |
| Panthenol | 5 g |
| Gum arabic | 8.5 g |
| Water | 7 g |
| Preservatives | qs |

Example 8

A waterproof mascara was prepared according to the following formula:

| | |
|---|---|
| Paraffin wax | 12 g |
| Stearic acid | 17 g |
| Starch | 1 g |
| Iron oxide | 5 g |
| Isoparaffin | 44.5 g |
| Montmorillonite | 10 g |
| Chitosonium carboxylate pyrrolidone, sold under the name "KYTAMER PC" by "AMERCHOL" | 1.5 g |
| Water | 9 g |
| Preservatives | qs |

Example 9

A waterproof mascara was prepared according to the following formula:

| | |
|---|---|
| Paraffin wax | 12 g |
| Oleic acid | 12 g |
| Vegetable oil | 6 g |
| Starch | 1 g |
| Iron oxide | 5 g |
| Isoparaffin | 41 g |
| Montmorillonite | 10 g |
| Hydroxy proline | 0.5 g |
| Cysteine | 0.5 g |
| Hydroxy-propyl-methyl cellulose, sold under the name "METHOCEL E" by "DOW CHEMICAL" | 2 g |
| Water | 10 g |
| Preservatives | qs |

Example 10

A waterproof mascara was prepared according to the following formula:

| | |
|---|---|
| Natural beeswax | 12 g |
| Paraffin | 10 g |
| Carnauba wax | 7 g |
| Starch | 2 g |
| Iron oxide | 5 g |
| Isoparaffin | 47.8 g |
| Montmorillonite | 7.5 g |
| Chitosan glutamate, sold under the name "SEA CURE 110" by "PROTAN" | 0.7 g |
| Water | 8 g |
| Preservatives | qs |

Example 11 (Comparative)

86 users were asked to test the following two mascaras in succession, the applicators being identical:

1) Mascara A: conventional waterproof mascara, having the following formulation:

| | |
|---|---|
| Carnauba wax | 13.8 g |
| Lanolin alcohol | 17.2 g |
| Starch | 2.3 g |
| Iron oxide | 5.7 g |
| Isoparaffin | 51.8 g |
| Montmorillonite | 9.2 g |

2) Mascara B: mascara according to the invention corresponding to the formulation of mascara "A", with the addition of 10% by weight of an aqueous solution (dry matter content of 13% by weight) of a keratin hydrolysate, sold under the name "KERASOL" by "CRODA CHEMICALS".

They were then asked to give their opinion on different parameters and to mark these two mascaras out of ten, criterion by criterion and in general. The opinions expressed as percentages and the marks given are illustrated in the following Table:

| Parameters | | Mascara A % of opinions expressed | Mascara B % of opinions expressed |
|---|---|---|---|
| Ease of application | Easy | 51 | 71 |
| | Fairly easy | 19 | 14 |
| | Fairly difficult | 17 | 14 |
| | Difficult | 13 | 1 |
| | Average mark /10 | 6.36 | 7.40 |
| Filler | Good | 44 | 61 |
| | Too much | 20 | 22 |
| | Insufficient | 34 | 15 |
| | Irregular | 2 | 2 |
| | Average mark /10 | 6.03 | 7.06 |
| Stretching | Good | 46 | 64 |
| | Fairly good | 21 | 20 |
| | Insufficient | 22 | 12 |
| | "Non-existent" | 11 | 4 |
| | Average mark /10 | 6.42 | 7.45 |
| Bending | Good | 44 | 63 |
| | Average | 36 | 28 |
| | Insufficient | 20 | 9 |
| | Average mark /10 | 6.30 | 7.34 |

This table shows that, overall, mascara B is clearly preferred to mascara A.

Example 12 (Comparative)

The water resistance of different mascaras was compared.

The test carried out is based on the fact that the energy of the ultrasonic waves transmitted by the water results in cavitation on the made-up eyelash, thereby cleaning it. The advantage of this technique compared to the action of a current of water over the eyelash is speed.

The general method of operation is as follows:

5 human eyelashes from one subject are fixed by the roots to a sheet of cardboard. The eyelashes are made up by hand with a mascara and are left to dry for 15 minutes. They are then immersed in a container full of water and subjected to ultrasonic waves for 5 minutes, and then for a further 7 minutes. Photographs are taken before making up, just before immersion and after 10 minutes of immersion. Enlargement of the negatives followed by a planimetric study makes it possible to detect by means of comparison the mascara loss after 10 minutes.

This test was carried out on mascaras A and B as defined in Example 10 and on a mascara C (according to the invention), in which the solution of keratin hydrolysate having a dry matter content of 13% by weight of mascara B was replaced by an aqueous solution having a dry matter content of 3% by weight of a copolymer (quaternized hydroxyethyl cellulose/acrylic polymer) (ratio by weight 1/5). The percentage P of mascara loss from the eyelashes immersed in a container subjected to ultrasonic waves for 10 minutes according to the experimental procedure defined hereinabove was measured. The results are listed in the following table:

| Mascara | P |
|---|---|
| A | 45 |
| B | 23 |
| C | 18 |

The percentages of loss after 10 minutes show very good water-resistant properties for mascaras B and C according to the invention. It can be assumed that the water-soluble and film forming polymers incorporated according to the invention plasticize the structure of the mascara and increase its water resistance.

Example 13 (Comparative)

Comparison of the electron micrographs of eyelashes coated with mascaras A and B as defined in Example 10 showed that, in the case of mascara B according to the invention, after making up, the eyelash was covered in a more homogeneous and regular manner than in the case of mascara A.

Example 14 (Comparative)

Two mascaras D and E were prepared, containing as a film forming polymer chitosonium carboxylate pyrrolidone, sold under the name "KYTAMER PC" by "AMERCHOL", the polymer being introduced in the form of a solution in water in the case of mascara D and in anhydrous form in the case of mascara E.

These two mascaras had the following composition:

| Constituents | D | E |
|---|---|---|
| Paraffin wax | 22.0 | 24.20 |
| Stearic acid | 3.0 | 3.30 |
| Starch | 1.0 | 1.1 |
| Iron oxide | 5.0 | 5.5 |
| Isoparaffin | 48.50 | 53.50 |

-continued

| Constituents | D | E |
|---|---|---|
| Montmorillonite | 10.0 | 10.9 |
| Chitosonium carboxylate pyrrolidone, sold under the name "KYTMER PC" by "AMERCHOL" | 1.50 | 1.50 |
| Water | 9.00 | — |

Comparison of micrographs of a layer of mascara D and of mascara E showed that mascara D was a soft homogeneous paste, while mascara E was heterogeneous and displayed hard grains of non-solubilized film forming polymer.

We claim:

1. A waterproof composition for covering the eyelashes consisting essentially of from 2 to 40 percent by weight, based on the total weight of said composition, of at least one wax, from 5 to 15 percent by weight, based on the total weight of said composition, of at least one thickening agent, from 35 to 50 percent by weight, based on the total weight of said composition, of at least one volatile organic solvent and from 1 to 35 percent by weight based on the total weight of said composition of an aqueous solution of at least one water-soluble film-forming agent present in an aqueous solution in an amount between approximately 0.1 to 55 percent, said composition not containing an emulsifying agent.

2. The composition of claim 1 wherein said water-soluble film-forming agent is selected from the group consisting of a keratin derivative; an anionic, cationic, amphoteric or nonionic derivative of chitin or chitosan; a cellulose derivative; an acrylic polymer; an acrylic copolymer; a polyvinyl pyrrolidone copolymer; a vinyl copolymer; an ethylene polymer and an oxyethylenated silicone.

3. The composition of claim 1 wherein said wax is selected from the group consisting of an animal wax, a vegetable wax, a mineral wax, a synthetic wax, and fractions of a natural wax, said wax having a melting point ranging from 60 to 110° C. and a needle penetration value at 25° C. ranging from 3 to 40 as measured by ASTM D5 or NFT 004.

4. The composition of claim 3 wherein said wax is solid and rigid at a temperature below 50° C.

5. The composition of claim 1 wherein said thickening agent is an organically modified clay.

6. The composition of claim 1 wherein said volatile organic solvent is selected from the group consisting of isoparaffin, turpentine oil, isopropyl alcohol, ethyl alcohol, white spirit and a volatile silicone derivative.

7. The composition of claim 1 which also includes up to 10 percent by weight, based on the total weight of said composition, of at least one powder filler selected from the group consisting of talc, starch, kaolin and a polyamide.

8. The composition of claim 1 which also includes up to 20 percent by weight, based on the total weight of said composition, of at least one pigment selected from the group consisting of a mineral pigment, an organic pigment, a pearl pigment and a coated pigment.

9. The composition of claim 1 which also includes at least one additive for eyelash makeup compositions, said additive being selected from the group consisting of a softening agent, a preservative, a sequestering agent, a perfume, a binding agent, an oil, a silicone, a cohesive agent, a non-film forming polymer, an alkalizing agent, an acidifying agent, a vitamin and an amino acid.

10. In a wax based waterproof composition for covering the eyelashes containing a polymer, a thickening agent and a volatile organic solvent, wherein the improvement comprises said polymer being at least one water-soluble film-forming agent in an aqueous solution and present in an amount ranging from 0.1 to 55 percent by weight of said aqueous solution and said aqueous solution being present in an amount ranging from 1 to 35 percent by weight based on the total weight of said composition, said composition not containing an emulsifier.

* * * * *